(12) United States Patent
Chagas

(10) Patent No.: US 9,920,096 B2
(45) Date of Patent: Mar. 20, 2018

(54) BRADYKININ RECEPTOR MODULATORS AND USE THEREOF

(71) Applicant: Sepia Pesquisa e Desenvolvimento, Sao Paolo (BR)

(72) Inventor: Jair Ribeiro Chagas, Sao Paulo (BR)

(*) Notice: Subject to any disclaimer, the term of this patent is extended or adjusted under 35 U.S.C. 154(b) by 0 days.

(21) Appl. No.: 14/392,278

(22) PCT Filed: Jun. 24, 2014

(86) PCT No.: PCT/IB2014/001162
§ 371 (c)(1),
(2) Date: Dec. 23, 2015

(87) PCT Pub. No.: WO2014/207534
PCT Pub. Date: Dec. 31, 2014

(65) Prior Publication Data
US 2016/0176929 A1    Jun. 23, 2016

(30) Foreign Application Priority Data
Jun. 25, 2013    (CH) ................................. 1168/13

(51) Int. Cl.
*C07K 7/18*    (2006.01)

(52) U.S. Cl.
CPC ...................................... *C07K 7/18* (2013.01)

(58) Field of Classification Search
None
See application file for complete search history.

(56) References Cited

U.S. PATENT DOCUMENTS

| | | | | |
|---|---|---|---|---|
| 4,693,993 | A | 9/1987 | Stewart et al. | |
| 7,045,133 | B2 * | 5/2006 | Achen .................... | C07K 14/52 424/185.1 |
| 2013/0136717 | A1 * | 5/2013 | Hillmeister ............ | A61K 38/04 424/85.1 |

FOREIGN PATENT DOCUMENTS

| | | |
|---|---|---|
| JP | H07330795 A | 12/1995 |
| JP | 2001002586 A | 1/2001 |
| WO | WO 93/25576 A2 | 12/1993 |
| WO | WO 98/07746 | 2/1998 |
| WO | WO 2010/111625 A1 | 9/2010 |

OTHER PUBLICATIONS

European Patent Application No. EP 14818114, by Sepia Pesquisa E Desenvolvimento: Supplementary European Search Report, dated Nov. 17, 2016 (4 pages).
European Patent Application No. EP 14818114, by Sepia Pesquisa E Desenvolvimento: Supplementary European Search Opinion, dated Nov. 25, 2016 (8 pages).
Swiss Patent Application No. CH01168/13, by Jair Ribeiro Chagas: Search Report, dated Sep. 24, 2013 (2 pages).
Dixon et al., "The Bradykinin $B_2$ Receptor Is a Delayed Early Response Gene for Platelet-derived Growth Factor in Arterial Smooth Muscle Cells," *The Journal of Biological Chemistry*, 271(23): 13324-13332 (1996).
Ikeda et al., "Host Stromal Bradykinin $B_2$ Receptor Signaling Facilities Tumor-Associated Angiogenesis and Tumor Growth," *Cancer Research*, 64: 5178-5185 (2004).
Joukov et al., "A novel vascular endothelial growth factor, VEGF-C, is a ligand for the Flt4 (VEGFR-3) and KDR (VEGFR-2) receptor tyrosine kinases," *The EMBO Journal*, 15(2): 290-298 (1996).
Sanchez De Miguel et al., "B2-kinin receptor plays a key role in B1-, angiotensin converting enzyme inhibitor-, and vascular endothelial growth factor-stimulated in vitro angiogenesis in the hypoxic mouse heart," *Cardiovascular Research*, 80: 106-113 (2008).
Stewart et al., "Bradykinin antagonists as new drugs for prostate cancer," *International Immunopharmacology*, 2: 1781-1786 (2002).
Vasquez-Pinto et al., "Bradykinin $B_1$ receptor antagonist R954 inhibits eosinophil activation/proliferation/migration and increases TGF-β and VEGF in a murine model of asthma," *Neuropeptides*, 44: 107-113 (2010).
International Patent Application No. PCT/IB2014/001162, by Sepia Pesquisa E Desenvolvimento: International Preliminary Report on Patentability, dated Aug. 18, 2015 (9 pages).
International Patent Application No. PCT/IB2014/001162, by Sepia Pesquisa E Desenvolvimento: International Search Report, dated Jan. 12, 2015 (6 pages).
International Patent Application No. PCT/IB2014/001162, by Sepia Pesquisa E Desenvolvimento: Written Opinion of the International Searching Authority, dated Jan. 12, 2015 (6 pages).
Fortin et al., "Advances in the development of bradykinin receptor ligands," *Current Topics in Medicinal Chemistry*, 6(13): 1353-1363 (2006).
Marceau et al., "Bradykinin receptor ligands: therapeutic perspectives," *Nature Reviews Drug Discovery*, 3(10): 845-852 (2004).
Moreau et al., "The Kallikrein-Kinin System: Current and Future Pharmacological Targets," *J. Pharmacol. Sci.*, 99: 6-38 (2005).

* cited by examiner

*Primary Examiner* — Maury Audet
(74) *Attorney, Agent, or Firm* — Finnegan, Henderson, Farabow, Garrett & Dunner LLP

(57) ABSTRACT

The present invention relates generally to novel biological and purified peptides as bradykinin receptor modulators for use in the treatment and/or prevention of inflammatory diseases, pain, hyperalgesia, cardiovascular and/or cerebral ischemic diseases, in a subject in need thereof.

7 Claims, 10 Drawing Sheets

```
                         SEQUENCE LISTING

<160> NUMBER OF SEQ ID NOS: 56

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Lys Pro Pro Cys Val Asn Val Phe Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Lys Pro Pro Cys Val Ser Val Tyr Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Trp Pro Pro Cys Val Glu Val Lys Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Trp Pro Pro Cys Val Glu Val Gln Arg
1               5                   10
```

```
<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Val Pro Ser Cys Val Thr Val Gln Arg
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Lys Pro Ser Cys Val Pro Leu Met Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Phe Ser Pro Ser Cys Val Ser Leu Leu Arg
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Pro Pro Cys Val Asn Val Phe Arg
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Pro Pro Cys Val Ser Val Tyr Arg
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10
```

Trp Pro Pro Cys Val Glu Val Lys Arg
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Pro Pro Cys Val Glu Val Gln Arg
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Pro Ser Cys Val Thr Val Gln Arg
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Pro Ser Cys Val Pro Leu Met Arg
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Pro Ser Cys Val Ser Leu Leu Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Lys Pro Pro Cys Val Asn Val Phe
1               5

<210> SEQ ID NO 16
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 16

Phe Lys Pro Pro Cys Val Ser Val Tyr
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Trp Pro Pro Cys Val Glu Val Lys
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Trp Pro Pro Cys Val Glu Val Gln
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Val Pro Ser Cys Val Thr Val Gln
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Lys Pro Ser Cys Val Pro Leu Met
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Ser Pro Ser Cys Val Ser Leu Leu
1               5
```

```
<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Pro Pro Cys Val Asn Val Phe
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Pro Pro Cys Val Ser Val Tyr
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Pro Pro Cys Val Glu Val Lys
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Trp Pro Pro Cys Val Glu Val Gln
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Val Pro Ser Cys Val Thr Val Gln
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 27

Lys Pro Ser Cys Val Pro Leu Met
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Pro Ser Cys Val Ser Leu Leu
1               5

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Ser Thr Asn Thr Phe Phe Lys Pro Pro Cys Val Asn Val Phe Arg
1               5                   10                  15

Cys Gly Gly Cys
            20

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Ala Thr Asn Thr Phe Phe Lys Pro Pro Cys Val Ser Val Tyr Arg
1               5                   10                  15

Cys Gly Gly Cys
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Ser Ala Asn Phe Leu Ile Trp Pro Pro Cys Val Glu Val Lys Arg
1               5                   10                  15

Cys Thr Gly Cys
            20

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 32

Thr Asn Ala Asn Phe Leu Val Trp Pro Pro Cys Val Glu Val Gln Arg
1               5                   10                  15

Cys Ser Gly Cys
            20

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Thr Val Ala Lys Gln Leu Val Pro Ser Cys Val Thr Val Gln Arg
1               5                   10                  15

Cys Gly Gly Cys
            20

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Glu Ile Glu Tyr Ile Phe Lys Pro Ser Cys Val Pro Leu Met Arg
1               5                   10                  15

Cys Gly Gly Cys
            20

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Glu Val Glu His Met Phe Ser Pro Ser Cys Val Ser Leu Leu Arg
1               5                   10                  15

Cys Thr Gly Cys
            20

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Ser Thr Asn Thr Phe Phe Lys Pro Pro Cys Val Asn Val Phe Pro
1               5                   10                  15

Pro Gly Gly Cys
            20

<210> SEQ ID NO 37
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Ala Thr Asn Thr Phe Phe Lys Pro Pro Cys Val Ser Val Tyr Pro
1               5                   10                  15

Pro Gly Gly Cys
            20

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Ser Ala Asn Phe Leu Ile Trp Pro Pro Cys Val Glu Val Lys Pro
1               5                   10                  15

Pro Thr Gly Cys
            20

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Asn Ala Asn Phe Leu Val Trp Pro Pro Cys Val Glu Val Gln Pro
1               5                   10                  15

Pro Ser Gly Cys
            20

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Thr Val Ala Lys Gln Leu Val Pro Ser Cys Val Thr Val Gln Pro
1               5                   10                  15

Pro Gly Gly Cys
            20

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Glu Ile Glu Tyr Ile Phe Lys Pro Ser Cys Val Pro Leu Met Pro
1               5                   10                  15
```

```
Pro Gly Gly Cys
        20

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Glu Val Glu His Met Phe Ser Pro Ser Cys Val Ser Leu Leu Pro
1               5                   10                  15

Pro Thr Gly Cys
        20

<210> SEQ ID NO 43
<211> LENGTH: 354
<212> TYPE: PRT
<213> ORGANISM: Homo sapiens

<400> SEQUENCE: 43

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
                20                  25                  30

Ser Gln Ser Thr Leu Glu Arg Ser Glu Gln Gln Ile Arg Ala Ala Ser
            35                  40                  45

Ser Leu Glu Glu Leu Leu Arg Ile Thr His Ser Glu Asp Trp Lys Leu
        50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Pro Pro Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270
```

```
Cys Lys Thr Pro Cys Pro Lys Asp Leu Ile Gln His Pro Lys Asn Cys
            275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

<210> SEQ ID NO 44
<211> LENGTH: 419
<212> TYPE: PRT
<213> ORGANISM: Homo sapiens

<400> SEQUENCE: 44

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Pro Pro Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285
```

```
Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
                355                 360                 365

Cys Leu Leu Lys Gly Lys Lys Phe His His Gln Thr Cys Ser Cys Tyr
        370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 45
<211> LENGTH: 211
<212> TYPE: PRT
<213> ORGANISM: Homo sapiens

<400> SEQUENCE: 45

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
                20                  25                  30

Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
        50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
                100                 105                 110

Thr Ser Ala Asn Phe Leu Ile Trp Pro Pro Cys Val Glu Val Lys Pro
            115                 120                 125

Pro Thr Gly Cys Cys Asn Thr Ser Ser Val Lys Cys Gln Pro Ser Arg
        130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
        195                 200                 205

Lys Pro Thr
    210

<210> SEQ ID NO 46
<211> LENGTH: 241
```

<212> TYPE: PRT
<213> ORGANISM: Homo sapiens

<400> SEQUENCE: 46

```
Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Pro Pro Ser Gly Cys Cys Asn Asn Arg Asn Val Gln Cys Arg Pro Thr
130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
210                 215                 220

Lys Phe Lys His Thr His Asp Lys Thr Ala Leu Lys Glu Thr Leu Gly
225                 230                 235                 240

Ala
```

<210> SEQ ID NO 47
<211> LENGTH: 207
<212> TYPE: PRT
<213> ORGANISM: Homo sapiens

<400> SEQUENCE: 47

```
Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
```

```
                100               105               110
    Glu Met Ser Leu Glu Glu His Ser Gln Cys Glu Cys Arg Pro Lys Lys
                    115               120               125

Lys Asp Ser Ala Val Lys Pro Asp Arg Ala Ala Thr Pro His His Arg
        130               135               140

Pro Gln Pro Arg Ser Val Pro Gly Trp Asp Ser Ala Pro Gly Ala Pro
    145               150               155               160

Ser Pro Ala Asp Ile Thr His Pro Thr Pro Ala Pro Gly Pro Ser Ala
                    165               170               175

His Ala Ala Pro Ser Thr Thr Ser Ala Leu Thr Pro Gly Pro Ala Ala
                    180               185               190

Ala Ala Ala Asp Ala Ala Ala Ser Val Ala Lys Gly Gly Ala
                    195               200               205

<210> SEQ ID NO 48
<211> LENGTH: 232
<212> TYPE: PRT
<213> ORGANISM: Homo sapiens

<400> SEQUENCE: 48

Met Asn Phe Leu Leu Ser Trp Val His Trp Ser Leu Ala Leu Leu Leu
    1               5                   10                  15

Tyr Leu His His Ala Lys Trp Ser Gln Ala Ala Pro Met Ala Glu Gly
                    20                  25                  30

Gly Gly Gln Asn His His Glu Val Val Lys Phe Met Asp Val Tyr Gln
                    35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
    65                  70                  75                  80

Met Pro Pro Gly Gly Cys Cys Asn Asp Glu Gly Leu Glu Cys Val Pro
                    85                  90                  95

Thr Glu Glu Ser Asn Ile Thr Met Gln Ile Met Arg Ile Lys Pro His
                    100                 105                 110

Gln Gly Gln His Ile Gly Glu Met Ser Phe Leu Gln His Asn Lys Cys
                    115                 120                 125

Glu Cys Arg Pro Lys Lys Asp Arg Ala Arg Gln Glu Lys Lys Ser Val
        130                 135                 140

Arg Gly Lys Gly Lys Gly Gln Lys Arg Lys Arg Lys Lys Ser Arg Tyr
    145                 150                 155                 160

Lys Ser Trp Ser Val Tyr Val Gly Ala Arg Cys Cys Leu Met Pro Trp
                    165                 170                 175

Ser Leu Pro Gly Pro His Pro Cys Gly Pro Cys Ser Glu Arg Arg Lys
                    180                 185                 190

His Leu Phe Val Gln Asp Pro Gln Thr Cys Lys Cys Ser Cys Lys Asn
                    195                 200                 205

Thr Asp Ser Arg Cys Lys Ala Arg Gln Leu Glu Leu Asn Glu Arg Thr
        210                 215                 220

Cys Arg Cys Asp Lys Pro Arg Arg
    225                 230

<210> SEQ ID NO 49
<211> LENGTH: 221
<212> TYPE: PRT
<213> ORGANISM: Homo sapiens
```

-continued

```
<400> SEQUENCE: 49

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Pro Pro Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg His Ser Pro Gly Arg Gln Ser Pro Asp Met Pro Gly Asp
    130                 135                 140

Phe Arg Ala Asp Ala Pro Ser Phe Leu Pro Pro Arg Arg Ser Leu Pro
145                 150                 155                 160

Met Leu Phe Arg Met Glu Trp Gly Cys Ala Leu Thr Gly Ser Gln Ser
                165                 170                 175

Ala Val Trp Pro Ser Ser Pro Val Pro Glu Glu Ile Pro Arg Met His
            180                 185                 190

Pro Gly Arg Asn Gly Lys Lys Gln Gln Arg Lys Pro Leu Arg Glu Lys
        195                 200                 205

Met Lys Pro Glu Arg Cys Gly Asp Ala Val Pro Arg Arg
    210                 215                 220

<210> SEQ ID NO 50
<211> LENGTH: 354
<212> TYPE: PRT
<213> ORGANISM: Homo sapiens

<400> SEQUENCE: 50

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140
```

-continued

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
                260                 265                 270

Cys Lys Thr Pro Cys Pro Lys Asp Leu Ile Gln His Pro Lys Asn Cys
            275                 280                 285

Ser Cys Phe Glu Cys Lys Glu Ser Leu Glu Thr Cys Cys Gln Lys His
        290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
                340                 345                 350

Asn Pro

<210> SEQ ID NO 51
<211> LENGTH: 419
<212> TYPE: PRT
<213> ORGANISM: Homo sapiens

<400> SEQUENCE: 51

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
                20                  25                  30

Glu Ser Gly Leu Asp Leu Ser Asp Ala Glu Pro Asp Ala Gly Glu Ala
            35                  40                  45

Thr Ala Tyr Ala Ser Lys Asp Leu Glu Glu Gln Leu Arg Ser Val Ser
        50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
                100                 105                 110

His Tyr Asn Thr Glu Ile Leu Lys Ser Ile Asp Asn Glu Trp Arg Lys
            115                 120                 125

Thr Gln Cys Met Pro Arg Glu Val Cys Ile Asp Val Gly Lys Glu Phe
        130                 135                 140

Gly Val Ala Thr Asn Thr Phe Phe Lys Pro Pro Cys Val Ser Val Tyr
145                 150                 155                 160

```
Arg Cys Gly Gly Cys Cys Asn Ser Glu Gly Leu Gln Cys Met Asn Thr
            165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
            195                 200                 205

Cys Arg Cys Met Ser Lys Leu Asp Val Tyr Arg Gln Val His Ser Ile
            210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
            245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
            275                 280                 285

Glu Thr Cys Gln Cys Val Cys Arg Ala Gly Leu Arg Pro Ala Ser Cys
            290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
            325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
            355                 360                 365

Cys Leu Leu Lys Gly Lys Lys Phe His His Gln Thr Cys Ser Cys Tyr
370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
            405                 410                 415

Gln Met Ser

<210> SEQ ID NO 52
<211> LENGTH: 211
<212> TYPE: PRT
<213> ORGANISM: Homo sapiens

<400> SEQUENCE: 52

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
            50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
            85                  90                  95

Lys Thr Arg Thr Val Ile Tyr Glu Ile Pro Arg Ser Gln Val Asp Pro
            100                 105                 110
```

```
Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
        130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
        195                 200                 205

Lys Pro Thr
    210

<210> SEQ ID NO 53
<211> LENGTH: 241
<212> TYPE: PRT
<213> ORGANISM: Homo sapiens

<400> SEQUENCE: 53

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala

<210> SEQ ID NO 54
<211> LENGTH: 207
```

<212> TYPE: PRT
<213> ORGANISM: Homo sapiens

<400> SEQUENCE: 54

Met Ser Pro Leu Leu Arg Arg Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Arg Ala Ala Thr Pro His His Arg
130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
        195                 200                 205

<210> SEQ ID NO 55
<211> LENGTH: 232
<212> TYPE: PRT
<213> ORGANISM: Homo sapiens

<400> SEQUENCE: 55

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

```
Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
            165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230
```

<210> SEQ ID NO 56
<211> LENGTH: 221
<212> TYPE: PRT
<213> ORGANISM: Homo sapiens

<400> SEQUENCE: 56

```
Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Pro Phe Gln Glu Val Trp Gly
            35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
            115                 120                 125

Glu Cys Arg His Ser Pro Gly Arg Gln Ser Pro Asp Met Pro Gly Asp
    130                 135                 140

Phe Arg Ala Asp Ala Pro Ser Phe Leu Pro Pro Arg Arg Ser Leu Pro
145                 150                 155                 160

Met Leu Phe Arg Met Glu Trp Gly Cys Ala Leu Thr Gly Ser Gln Ser
                165                 170                 175

Ala Val Trp Pro Ser Ser Pro Val Pro Glu Glu Ile Pro Arg Met His
            180                 185                 190

Pro Gly Arg Asn Gly Lys Lys Gln Gln Arg Lys Pro Leu Arg Glu Lys
            195                 200                 205

Met Lys Pro Glu Arg Cys Gly Asp Ala Val Pro Arg Arg
    210                 215                 220
```

BRADYKININ RECEPTOR MODULATORS AND USE THEREOF

This application is the national stage entry under 35 U.S.C. § 371 of International Application No. PCT/IB2014/001162, filed on Jun. 24, 2014, which claims priority to Swiss Application No. 01168/13, filed Jun. 25, 2013. The contents of these applications are each incorporated herein by reference in their entirety.

TECHNICAL FIELD

The present invention relates generally to novel biological and purified peptides as bradykinin receptor modulators for use in the treatment and/or prevention of inflammatory diseases, pain, hyperalgesia, cardiovascular and/or cerebral ischemic diseases, in a subject in need thereof.

SEQUENCE LISTING

The instant application contains a Sequence Listing which has been submitted electronically in ASCII format and is hereby incorporated by reference in its entirety. Said ASCII copy, created on Feb. 9, 2016, is named 13239.0001-00000_SL.txt and is 44,191 bytes in size.

BACKGROUND OF THE INVENTION

Angiogenesis is the development of new blood capillaries and vessels. This process occurs normally in a number of biological situations, including fetal development, menstruation, ovulation, placental development and the development of collateral blood vessels in areas of disease or ischemia, nerve regeneration, bone growth, and wound healing. All these events, especially fetal development, require the very rapid growth of endothelial cells and their migration and differentiation into a complex network of vessels.

In addition to angiogenesis, which takes place in the healthy individual, angiogenic events are involved in a number of pathological processes, notably tumor growth and metastasis, and other conditions in which blood vessels proliferation, especially of the microvascular system, is increased, such as diabetic retinopathy, psoriasis and arthropathies. Inhibition of angiogenesis is useful in preventing or alleviating these pathological processes.

Because of the crucial role of angiogenesis in so many physiological and pathological processes, factors involved in the control of angiogenesis have been intensively investigated.

Vascular endothelial cell growth factor (VEGF), which is also termed VEGF-A or vascular permeability factor (VPF), has been reported as a pivotal regulator of both normal and abnormal angiogenesis (Ferrara and Davis-Smyth, 1997; Ferrara, 1999). In addition, truncated forms of VEGF-D and VEGF-C have been shown to stimulate angiogenesis through binding to VEGFR-2 (WO2012/088563).

The stimulation of angiogenesis has also been shown with agonistic substances of Bradykinin B1 and B2 receptors (WO 02/17958).

Bradykinin (BK) is a nonapeptide of sequence Arg-Pro-Pro-Gly-Phe-Ser-Pro-Phe-Arg, generated as a result of the activity of kallikreins, a group of proteolytic enzymes present in most tissues and body fluids, on kininogens. BK and related kinins, like Lys-BK (kallidin) and Met-Lys-BK are able to activate the bradykinin B2 receptor. The removal of the C-terminal Arg residue in BK or in kallidin (Lys-BK) generates desArg9-BK and desArg9-Lys-BK. These peptides are also kinins and are specific ligands of the bradykinin B1 receptor. Once released, kinins produce many physiological responses, including pain and hyperalgesia by stimulating C- and A-fibers in the periphery. There is also considerable evidence that kinins contribute to the inflammatory response.

Bradykinin, and its physiologically important related peptides described above exhibit physiological actions which qualify them as mediators of inflammatory reactions, hypotensive states, pain, hyperalgesia, cardiovascular and/or cerebral circulatory diseases, tissue repair, stem cell differentiation, angiogenesis, lymphangiogenesis, immune system cells modulation, sepsis, wasting states, diabetes, neurogenesis, cardiac function and remodeling, kidney function, neurogenesis, and tumor development (Marceau F. and Regoli D., 2004).

Although treatments exist, there remain significant unmet needs for efficient and better therapies for activating or inhibiting angiogenesis and preventing and/or treating inflammatory diseases, pain, hyperalgesia, cardiovascular and/or cerebral ischemic diseases, notably in term of improved efficacy, and diminution of side effects.

SUMMARY OF THE INVENTION

The present invention provides an isolated and purified peptide selected from the group consisting of:
a) a peptide having an amino acid sequence selected from the group consisting of SEQ ID NO:1 to SEQ ID NO:7;
b) a biological fragment thereof having at least 8 consecutive residues in length.

The present invention also provides an isolated and purified peptide selected from the group consisting of:
a) a biological variant having an amino acid sequence selected from the group consisting of SEQ ID NO:43 to SEQ ID NO:49;
b) a biological fragment thereof having an amino acid sequence selected from the group consisting of SEQ ID NO:36 to SEQ ID NO:42;
characterized in that said isolated and purified peptide is a Bradykinin receptor modulator.

Also disclosed is an isolated and purified nucleic acid molecule encoding an isolated and purified peptide, a vector comprising said nucleic acid molecule, a recombinant host cell characterized in that said cell expresses an isolated and purified peptide of the invention.

Further disclosed is a pharmaceutical composition comprising an isolated and purified peptide according to the invention, the use of said pharmaceutical compositions as analgesics, and the use of said pharmaceutical compositions in the treatment and/or prevention of inflammatory diseases, cardiovascular ischemia, pain, hyperalgesia, renal diseases, wound healing, cerebral ischemia, stroke, vascular dementia, infarct dementia, myocardial ischemia, coronary heart disease, myocardial infarction, peripheral limb disease, periphery arterial occlusive disease, sepsis, wasting states, diabetes and/or disorders associated with defective blood flow or blood vessel malformation, tissue repair, stem cell differentiation, angiogenesis, lymphangiogenesis, immune system cells modulation.

BRIEF DESCRIPTION OF THE FIGURES

FIG. 5A: A.F.U.—Arbitrary Fluorescence Units; BK 1 μM Bradykinin; THG Thapsigargin 10 μM. FIG. 5B: PepD 2-10 at 10 μM; THG Thapsigargin 10 μM. FIG. 5C: HOE 140 (B2 receptor antagonist) 10 μM; PepD 2-10 10 μM; THG Thapsigargin 10 μM. FIG. 5D: DesArg9-Leu8-BK 10 μM; PepD 2-10 10 μM; THG Thapsigargin 10 μM. FIG. 5E: PepPL 1-10 (SEQ ID NO:7).

DETAILED DESCRIPTION OF THE INVENTION

Figure 1:
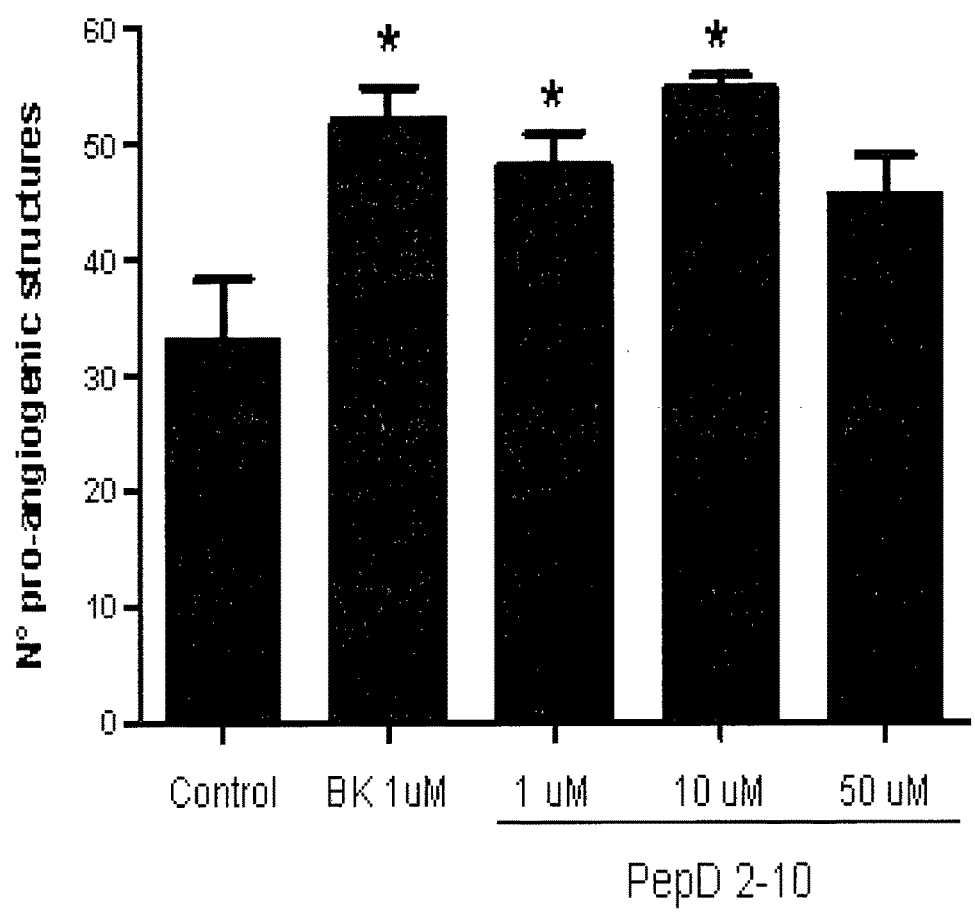
FIG. 1 shows the effect of 1 μM Bradykinin (BK) and of different concentrations of the peptide PepD 2-10 (KPP-CVNVFR; SEQ ID NO:8), corresponding to the amino acid residues number 133-141 from human VEGF-D sequence registered at Expasy (http://www.uniprot.org/uniprot/O43915), on the HUVEC angiogenesis assay. * p<0.05 compared to control (Student's "t" test).

Growth factors are naturally occurring substances capable of stimulating cellular growth, proliferation and cellular differentiation. Growth factors are important for regulating a variety of cellular processes. Growth factors typically act as signaling molecules between cells. For example, bone morphogenetic proteins stimulate bone cell differentiation, while fibroblast growth factors and vascular endothelial growth factors stimulate angiogenesis and blood vessel differentiation.

Individual growth factor proteins tend to occur as members of larger families of structurally and evolutionarily related proteins. For example, placental growth factor (PlGF, UNIPROT accession number P49763), Vascular endothelial growth factor (VEGF-A, UNIPROT accession number P15692; VEGF-B, UNIPROT accession number P49765; VEGF-C, UNIPROT accession number P49767 and VEGF-D, UNIPROT accession number O43915), and Platelet-derived growth factor (PDGF-A, UNIPROT accession number P04085; PDGF-B, UNIPROT accession number P01127).

In one aspect, the present invention provides an isolated and purified peptide selected from the group consisting of:
a) a biological variant having an amino acid sequence selected from the group consisting of SEQ ID NO:43 to SEQ ID NO:49;
b) a biological fragment thereof having an amino acid sequence selected from the group consisting of SEQ ID NO:36 to SEQ ID NO:42;

In another aspect, the present invention provides an isolated and purified peptide selected from the group consisting of:
a) a biological variant having an amino acid sequence selected from the group consisting of SEQ ID NO:43 to SEQ ID NO:49;
b) a biological fragment thereof having an amino acid sequence selected from the group consisting of SEQ ID NO:36 to SEQ ID NO:42;
wherein said isolated and purified peptide is a Bradykinin receptor modulator.

As used herein, the terms "peptide", "protein", "polypeptide", "polypeptidic", and "peptidic" are used interchangeably herein to designate a series of amino acid residues connected to the other by peptide bonds between the alpha-amino and carboxy groups of adjacent residues.

The present invention also includes biological variants of the isolated and purified peptide. The term "biological variants" refer to polypeptides having amino acid sequences that differ to some extent from a native sequence of the isolated and purified peptide that is amino acid sequences that vary from the native sequence by conservative amino acid substitutions, whereby one or more amino acids are substituted by another with same characteristics and conformational roles. The amino acid sequence variants possess substitutions, and/or insertions at certain positions within the amino acid sequence of the native amino acid sequence. Conservative amino acid substitutions are herein defined as exchanges within one of the following five groups:

I. Small aliphatic, nonpolar or slightly polar residues: Ala, Ser, Thr, Pro, Gly
II. Polar, positively charged residues: His, Arg, Lys
III. Polar, negatively charged residues: and their amides: Asp, Asn, Glu, Gln
IV. Large, aromatic residues: Phe, Tyr, Trp
V. Large, aliphatic, nonpolar residues: Met, Leu, Ile, Val, Cys.

As used herein, "biological variants" have a mutation, and/or a substitution of at least one residue in an amino acid sequence selected from the group consisting of SEQ ID NO:50 to SEQ ID NO:56. Preferably, said biological variants consist of SEQ ID NO:36 to SEQ ID NO:49. More preferably said biological variants are Bradykinin receptor modulators. Even more preferably, said biological variants are anti-angiogenics.

In a further aspect, the present invention provides an isolated and purified peptide selected from the group consisting of:
a) a peptide having an amino acid sequence selected from the group consisting of SEQ ID NO:1 to SEQ ID NO:7;
b) a biological fragment thereof having at least 8 consecutive residues in length.

The present invention also provides an isolated and purified peptide selected from the group consisting of:
a) a peptide having an amino acid sequence selected from the group consisting of SEQ ID NO: 1 to SEQ ID NO:7;
b) a biological fragment thereof having at least 8 consecutive residues in length;
wherein said isolated and purified peptide is a Bradykinin receptor modulator.

Preferably step b consists of biological fragments having an amino acid sequence selected from the group consisting of SEQ ID NO:8 to SEQ ID NO:28. More preferably, said biological fragments have Bradykinin receptor agonist activity.

"Biological fragments" refer to sequences sharing at least 50% amino acids in length with the respective sequence of the isolated and/or purified peptide. These sequences can be used as long as they exhibit the same properties as the native sequence from which they derive. Preferably these sequences share more than 70%, preferably more than 80%, in particular more than 90% amino acids in length with the respective sequence of the isolated and/or purified peptide. These fragments can be prepared by a variety of methods and techniques known in the art such as for example chemical synthesis.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

Furthermore, since an inherent problem with native peptides (in L-form) is the degradation by natural proteases, the peptide of the invention may be prepared in order to include D-forms and/or "retro-inverso isomers" of the peptide. Preferably, retro-inverso isomers of short parts, variants or combinations of the peptide of the invention are prepared.

Protecting the peptide from natural proteolysis should therefore increase the effectiveness of the isolated and purified peptide. A higher biological activity is predicted for the retro-inverso containing peptide when compared to the non-retro-inverso containing analog owing to protection from degradation by native proteinases. Furthermore, they have been shown to exhibit an increased stability and lower immunogenicity (Sela M. and Zisman E., 1997).

Retro-inverso peptides are prepared for peptides of known sequence as described for example in Sela and Zisman, 1997.

By "retro-inverso isomer" is meant an isomer of a linear peptide in which the direction of the sequence is reversed and the chirality of each amino acid residue is inverted; thus, there can be no end-group complementarity.

Also encompassed by the present invention are modifications of the peptide (which do not normally alter primary sequence), including in vivo or in vitro chemical derivatization of peptides, e. g., acetylation or carboxylation. Also included are modifications of glycosylation, e. g., those made by modifying the glycosylation patterns of a peptide during its synthesis and processing or in further processing steps, e. g., by exposing the peptide to enzymes which affect glycosylation e. g., mammalian glycosylating or deglycosylating enzymes. Also included are sequences which have phosphorylated amino acid residues, e. g., phosphotyrosine, phosphoserine, or phosphothreonine.

The term "isolated and purified" refers to the state in which the peptide of the invention, or nucleic acid encoding such peptide will be, in accordance with the present invention free or substantially free of material with which they are naturally associated such as other polypeptides or nucleic acids with which they are found in their natural environment, or the environment in which they are prepared (e. g. cell culture) when such preparation is by recombinant DNA technology practiced in vitro or in vivo.

In one embodiment, the present invention provides an isolated and purified peptide selected from the group consisting of SEQ ID NO:1 to SEQ ID NO:7 (Table I).

According to another embodiment of the present invention, the isolated and purified peptide selected from the group consisting of SEQ ID NO:1 to SEQ ID NO:7 is a bradykinin receptor modulator, preferably, a B2 bradykinin receptor modulator.

More preferably, the isolated and purified peptide selected from the group consisting of SEQ ID NO:1 to SEQ ID NO:7 is a B2 bradykinin receptor agonist.

TABLE I

| SEQ ID NO: | Amino acid sequence | Peptide Name | Derived from |
|---|---|---|---|
|  | RPPGFSPFR | BK |  |
| SEQ ID NO: 1 | FKPPCVNVFR | PepD 1-10 | VEGF-D |
| SEQ ID NO: 2 | FKPPCVSVYR | PepC 1-10 | VEGF-C |
| SEQ ID NO: 3 | IWPPCVEVKR | PepPDA 1-10 | PDGF-A |
| SEQ ID NO: 4 | VWPPCVEVQR | PepPDB 1-10 | PDGF-B |
| SEQ ID NO: 5 | LVPSCVTVQR | PepB 1-10 | VEGF-B |
| SEQ ID NO: 6 | FKPSCVPLMR | PepA 1-10 | VEGF-A |
| SEQ ID NO: 7 | FSPSCVSLLR | PepP1 1-10 | P1GF |

In another embodiment of the invention, the isolated and purified peptide is a biological fragment selected from the group consisting of SEQ ID NO:8 to SEQ ID NO:14 (Table II). According to a further embodiment, the isolated and purified peptide consists of a biological fragment having at least 8 consecutive residues in length and selected from the group consisting of SEQ ID NO:8 to SEQ ID NO:14. Said biological fragment is a bradykinin receptor modulator, preferably a B2 bradykinin receptor modulator.

More preferably, said isolated and purified peptide consisting of SEQ ID NO:8 to SEQ ID NO:14 is a B2 bradykinin receptor agonist.

TABLE II

| SEQ ID NO: | Amino acid sequence | Peptide name | Derived from |
|---|---|---|---|
| SEQ ID NO: 8 | KPPCVNVFR | PepD 2-10 | VEGF-D |
| SEQ ID NO: 9 | KPPCVSVYR | PepC 2-10 | VEGF-C |
| SEQ ID NO: 10 | WPPCVEVKR | PepPDA 2-10 | PDGF-A |
| SEQ ID NO: 11 | WPPCVEVQR | PepPDB 2-10 | PDGF-B |
| SEQ ID NO: 12 | VPSCVTVQR | PepB 2-10 | VEGF-B |
| SEQ ID NO: 13 | KPSCVPLMR | PepA 2-10 | VEGF-A |
| SEQ ID NO: 14 | SPSCVSLLR | PepP1 2-10 | P1GF |

In a subsequent embodiment of the invention, the isolated and purified peptide is a biological fragment selected from the group consisting of SEQ ID NO:15, to SEQ ID NO:21 (Table III). The latter is a bradykinin receptor modulator, preferably a B1 bradykinin receptor modulator. More preferably, said isolated and purified peptide is a B1 bradykinin receptor agonist.

TABLE III

| SEQ ID NO: | Amino acid sequence | Peptide name | Derived from |
|---|---|---|---|
| SEQ ID NO: 15 | FKPPCVNVF | PepD 1-9 | VEGF-D |
| SEQ ID NO: 16 | FKPPCVSVY | PepC 1-9 | VEGF-C |
| SEQ ID NO: 17 | IWPPCVEVK | PepPDA 1-9 | PDGF-A |
| SEQ ID NO: 18 | VWPPCVEVQ | PepPDB 1-9 | PDGF-B |
| SEQ ID NO: 19 | LVPSCVTVQ | PepB 1-9 | VEGF-B |
| SEQ ID NO: 20 | FKPSCVPLM | PepA 1-9 | VEGF-A |
| SEQ ID NO: 21 | FSPSCVSLL | PepP1 1-9 | P1GF |

In a further embodiment of the invention, the isolated and purified peptide consists in a biological fragment having at least 8 consecutive residues in length and selected from the group consisting of SEQ ID NO:22 to SEQ ID NO:28 (Table IV). Preferably said biological fragment is a B1 bradykinin receptor modulator. More preferably, said biological fragment is a B1 bradykinin receptor agonist.

TABLE IV

| SEQ ID NO: | Amino acid sequence | Peptide name | Derived from |
|---|---|---|---|
| SEQ ID NO: 22 | KPPCVNVF | PepD 2-9 | VEGF-D |
| SEQ ID NO: 23 | KPPCVSVY | PepC 2-9 | VEGF-C |
| SEQ ID NO: 24 | WPPCVEVK | PepPDA 2-9 | PDGF-A |
| SEQ ID NO: 25 | WPPCVEVQ | PepPDB 2-9 | PDGF-B |
| SEQ ID NO: 26 | VPSCVTVQ | PepB 2-9 | VEGF-B |
| SEQ ID NO: 27 | KPSCVPLM | PepA 2-9 | VEGF-A |
| SEQ ID NO: 28 | SPSCVSLL | PepP1 2-9 | P1GF |

In a further embodiment of the invention, the isolated and purified peptide consists of SEQ ID NO:1, SEQ ID NO:6, SEQ ID NO:8, SEQ ID NO:15, SEQ ID NO:20, or SEQ ID NO:27.

The present invention also provides an isolated and purified peptide selected from the group consisting of:
a) a biological variant having an amino acid sequence selected from the group consisting of SEQ ID NO:43 to SEQ ID NO:49;
b) a biological fragment thereof having an amino acid sequence selected from the group consisting of SEQ ID NO:36 to SEQ ID NO:42;
wherein said isolated and purified peptide is a Bradykinin receptor modulator.

According to another embodiment of the invention, the isolated and purified peptide consists in a biological variant selected from the group consisting of SEQ ID NO:36 to SEQ ID NO:49 (Table VI and VII).

Preferably, said biological variant is a Bradykinin receptor modulator. More preferably, said biological variant is anti-angiogenic and/or anti-lymphangiogenic.

The term "biological variants" refer to polypeptides having amino acid sequences that differ to some extent from a native sequence of the isolated and/or purified polypeptide that is amino acid sequences that vary from the native sequence by conservative amino acid substitutions, whereby one or more amino acids are substituted by another with same characteristics and conformational roles. The amino acid sequence variants possess substitutions, and/or insertions at certain positions within the amino acid sequence of the native amino acid sequence. Conservative amino acid substitutions are herein defined as exchanges within one of the following five groups:
I. Small aliphatic, nonpolar or slightly polar residues: Ala, Ser, Thr, Pro, Gly
II. Polar, positively charged residues: His, Arg, Lys
III. Polar, negatively charged residues: and their amides: Asp, Asn, Glu, Gln
IV. Large, aromatic residues: Phe, Tyr, Trp
V. Large, aliphatic, nonpolar residues: Met, Leu, Ile, Val, Cys.

As used herein, the term "anti-angiogenics" refers to any molecule inhibiting angiogenesis and/or lymphangiogenesis.

As used herein, the term "anti-lymphangiogenic" refers to any molecule inhibiting lymphangiogenesis related to lymphatic vessels growth.

According to a further aspect, the present invention provides an isolated and purified peptide having an amino acid sequence selected from the group consisting of SEQ ID NO:29 to SEQ ID NO:35 (Table V).

Preferably, said isolated and purified peptide gives rise, through proteolytic hydrolysis, to a Bradykinin receptor modulator. More preferably, said isolated and purified peptide generated by proteolytic hydrolysis is a Bradykinin receptor agonist.

TABLE V

| SEQ ID NO: | Amino acid sequence |
|---|---|
| SEQ ID NO: 29 | KSTNTF FKPPCVNVFR CGGC |
| SEQ ID NO: 30 | VATNTF FKPPCVSYR CGGC |
| SEQ ID NO: 31 | TSANFL IWPPCVEVKR CTGC |
| SEQ ID NO: 32 | TNANFL VWPPCVEVQR CSGC |
| SEQ ID NO: 33 | GTVAKQ LVPSCVTVQR CGGC |
| SEQ ID NO: 34 | DEIEYI FKPSCVPLMR CGGC |
| SEQ ID NO: 35 | SEVEHM FSPSCVSLLR CTGC |

According to a further aspect, the present invention provides an isolated and purified peptide consisting of a biological variant having an amino acid sequence selected from the group consisting of SEQ ID NO:36 to SEQ ID NO:42 (Table VI).

According to a preferred embodiment, said isolated and purified peptide is a Bradykinin receptor modulator.

According to a further aspect, it is provided an isolated and purified peptide consisting of SEQ ID NO:36 to SEQ ID NO:42 wherein said peptides are anti-angiogenics.

TABLE VI

| SEQ ID NO: | Amino acid sequence |
|---|---|
| SEQ ID NO: 36 | KSTNTF FKPPCVNVFP PGGC |
| SEQ ID NO: 37 | VATNTF FKPPCVSVYP PGGC |
| SEQ ID NO: 38 | TSANFL IWPPCVEVKP PTGC |

TABLE VI-continued

| SEQ ID NO: | Amino acid sequence |
|---|---|
| SEQ ID NO: 39 | TNANFL VWPPCVEVQP PSGC |
| SEQ ID NO: 40 | GTVAKQ LVPSCVTVQP PGGC |
| SEQ ID NO: 41 | DEIEYI FKPSCVPLMP PGGC |
| SEQ ID NO: 42 | SEVEHM FSPSCVSLLP PTGC |

According to a further aspect, the present invention provides an isolated and purified peptide consisting of a biological variant having an amino acid sequence selected from the group consisting of SEQ ID NO:43 to SEQ ID NO:49 wherein said peptide is a VEGF, PDGF or PlGF receptor modulator (Table VII).

Preferably, said isolated and purified peptide is anti-angiogenic.

TABLE VII

| SEQ ID NO: | Growth factors Variants |
|---|---|
| SEQ ID NO: 43 | Variant VEGF-D R141P; C142P |
| SEQ ID NO: 44 | Variant VEGF-C R161P; C162P |
| SEQ ID NO: 45 | Variant PDGF-A R128P; C129P |
| SEQ ID NO: 46 | Variant PDGF-B R129P; C130P |
| SEQ ID NO: 47 | Variant VEGF-B R77P; C78P |
| SEQ ID NO: 48 | Variant VEGF-A R82P; C83P |
| SEQ ID NO: 49 | Variant PlGF R82P; C83P |

TABLE VIII

| SEQ ID NO: | Human Growth factors |
|---|---|
| SEQ ID NO: 50 | VEGF-D |
| SEQ ID NO: 51 | VEGF-C |
| SEQ ID NO: 52 | PDGF-A |
| SEQ ID NO: 53 | PDGF-B |
| SEQ ID NO: 54 | VEGF-B |
| SEQ ID NO: 55 | VEGF-A |
| SEQ ID NO: 56 | PlGF |

In a further aspect, the present invention provides an isolated and purified peptide selected from the group consisting of:
a) a peptide having an amino acid sequence selected from the group consisting of SEQ ID NO: 1 to SEQ ID NO:7;
b) a biological fragment thereof having at least 8 consecutive residues in length;
wherein said isolated and purified peptide is a Bradykinin receptor modulator inducing calcium entry in endothelial cells expressing B1 or B2 bradykinin receptors.

Preferably step b is a biological fragment having an amino acid sequence selected from the group consisting of SEQ ID NO:8 to SEQ ID NO:28 wherein said isolated and purified peptide is a Bradykinin receptor modulator inducing calcium entry in endothelial cells expressing B1 or B2 bradykinin receptors.

In a further aspect, the present invention provides an isolated and purified peptide selected from the group consisting of:
a) a peptide having an amino acid sequence selected from the group consisting of SEQ ID NO:1 to SEQ ID NO:7;
b) a biological fragment thereof having at least 8 consecutive residues in length;
wherein said isolated and purified peptide is a Bradykinin receptor modulator inducing angiogenesis.

Other expected actions of B1 and B2 agonists are inflammatory reactions, hypotensive states, pain, hyperalgesia, cardiovascular and/or cerebral circulatory diseases, tissue repair, stem cell differentiation, angiogenesis, lymphangiogenesis, immune system cells modulation, sepsis, wasting states, diabetes, diabetic neuropathy, allergies, brain edema neurogenesis, cardiac function and remodeling, kidney salts balance function, neurogenesis, tumor development (Marceau F. and Regoli D., 2004; Trujillo C. A. et al., 2012).

Preferably step b is a biological fragment having an amino acid sequence selected from the group consisting of SEQ ID NO:8 to SEQ ID NO:28 wherein said isolated and purified peptide is a Bradykinin receptor modulator inducing angiogenesis.

The present invention also relates to peptides having Cys residues that can form dimers, homo or heterodimers, through S-S bridges, and these dimers can be active as homodimers or heterodimers (e.g., Seq ID No 8 dimer with itself or Seq ID No 8 dimer with Seq ID No 23, for example). The present invention considers also dimers obtained by other methods of homo or heterodimerization.

In another aspect, the present invention relates to any cyclic peptides of SEQ ID NO: 1 to SEQ ID NO:56.

The isolated and purified peptide of the present invention may be provided by chemical synthesis, obtained from a biotechnological method and/or extracted from a natural source.

Preferably, the isolated and purified peptide is provided by chemical synthesis. In the context of peptides, the term "chemical synthesis" may refer to SPPS, liquid phase peptide synthesis or a combination of both. Here, the synthesis typically bases on the stepwise coupling of amino acids bearing protected side chains (orthogonal protecting groups). Typically, during synthesis, the peptide strand grows from the C-terminus to the N-terminus. However, there are alternative methods wherein the peptide strand grows from the N-terminus to the C-terminus. Nowadays, the most common methods base on at least two different types of protecting groups that are cleavable under at least two different conditions, such as, e.g., the fluorenyl-9-methoxycarbonyl/tert-butanyl- (Fmoc/tBu) protecting group scheme (Sheppard Tactics) or the tert-butoxycarbonyl/benzyl- (Boc/Bzl) protecting group scheme (Merrifield Tactics). Alternatively or additionally, the peptide may be also provided by conjugating two or more peptide strand(s) with another by any conjugation method known in the art such as, e.g., Native Chemical Ligation (NCL), Click Chemistry, Maleimide-Thiol Conjugation, enzymatic conjugation, biochemical protein ligation and/or soluble handling conjugation.

Alternatively, the isolated and purified peptide may be obtained from a biotechnological method. Today, numerous biotechnological methods are well-known in the art such as, e.g., overexpression and/or heterologous expression, in particular heterologous expression based on cloning of one or more gene(s) in bacteria, insect cells, mammalian cells, plant cells or yeast cells. The isolated and purified peptide may further be extracted by any means known in the art.

Alternatively, the isolated and purified peptide may be extracted from a natural source by any means known in the art. Additionally, the isolated and purified peptide may be purified by any means known in the art, such as, e.g., one or more chromatographic method(s), one or more filtration method(s), one or more electrophoretic method(s), one or more precipitation-based method(s), due or more dialysis method(s) or a combination of two or more thereof. The natural source may be any biological material such as, e.g., bacterial material, plant material, animal material or fungal material, such as e.g. tissue, liquids or secretion(s). The isolated and purified peptide obtained from a natural source may also be digested or partly digested by one or more enzymes, such as protease(s).

It will be understood by a person skilled in the art, that the aforementioned methods for providing an isolated and purified peptide may also be combined with another. In particular, a bradykinin receptor agonist obtained from a biotechnological method or a natural source may further be purified and/or modified by chemical means known in the art.

According to a further aspect, the present invention provides an isolated and purified nucleic acid molecule encoding the isolated and purified peptide.

DNA which can be used herein is any polydeoxynucleotide, including, e.g. double-stranded DNA, single-stranded DNA, double-stranded DNA wherein one or both strands are composed of two or more fragments, double-stranded DNA wherein one or both strands have an uninterrupted phosphodiester backbone, DNA containing one or more single-stranded portion(s) and one or more double-stranded portion(s), double-stranded DNA wherein the DNA strands are fully complementary, double-stranded DNA wherein the DNA strands are only partially complementary, circular DNA, covalently-closed DNA, linear DNA, covalently cross-linked DNA, cDNA, chemically-synthesized DNA, semi-synthetic DNA, biosynthetic DNA, naturally-isolated DNA, enzyme-digested DNA, sheared DNA, labeled DNA, such as radiolabeled DNA and fluorochrome-labeled DNA, DNA containing one or more non-naturally occurring species of nucleic acid.

DNA sequences that encode the isolated and purified peptide, or a part thereof, can be synthesized by standard chemical techniques, for example, the phosphotriester method or via automated synthesis methods and PCR methods. The purified and isolated DNA sequence encoding the isolated and purified peptide according to the invention may also be produced by enzymatic techniques. Thus, restriction enzymes, which cleave nucleic acid molecules at predefined recognition sequences can be used to isolate nucleic acid sequences from larger nucleic acid molecules containing the nucleic acid sequence, such as DNA (or RNA) that codes for the isolated and purified peptide or a part thereof.

The present invention also includes variants of the aforementioned sequences, that is nucleotide sequences that vary from the reference sequence by conservative nucleotide substitutions, whereby one or more nucleotides are substituted by another with same characteristics.

According to a preferred embodiment, the inventions concerns an isolated and purified cDNA molecule encoding the isolated and purified peptides of the invention.

As used herein, the term "cDNA" refers to complementary DNA that is a single stranded DNA complementary to messenger RNA, a DNA synthesized from messenger RNA by reverse transcriptase and/or double stranded complementary DNA synthesized from messenger RNA suitable for subsequent ligation into an expression vector.

Another subject matter of the present invention is a vector comprising the nucleic acid molecule of the invention. The vector being capable of replication in eukaryotes, prokaryotes or in eukaryotes and prokaryotes. It can be a vector capable of integration into the genome of the host cell (e.g. bacteriophage lambda) or a vector which is present extra-chromosomally (e.g. a plasmid). Preferably, the vector is a plasmid.

Further, the vector can be an expression vector, i.e. a vector in which the isolated and purified DNA sequence is operably linked to a promoter. This means that the linked isolated and purified DNA sequence encoding the isolated and purified peptide of the present invention is under control of a suitable regulatory sequence which allows expression, i.e. transcription and translation of the inserted isolated and purified DNA sequence. Suitable expression vectors for prokaryotic host cells are described in Sambrook et al., Molecular Cloning; a Laboratory Manual, 2nd Edition (1989), Cold Spring Harbor Laboratory Press, especially in Chapters 1-4 and 17. Suitable vectors for expression of cloned genes in mammalian cells are described in Sambrook et al., Chapter 16. Suitable vectors can be chosen or constructed, containing appropriate regulatory sequences, including promoter sequences, terminator sequences, polyadenylation sequences, marker genes and other sequences as appropriate.

According to a preferred embodiment of the invention, the expression vector comprises at least one copy of the isolated and purified cDNA molecule encoding the isolated and purified peptide of the invention.

The terms "introducing a purified DNA into a eukaryotic or prokaryotic host cell" or "transfection" denote any process wherein an extracellular DNA, with or without accompanying material, enters a host cell. The term "cell transfected" or "transfected cell" means the cell into which the extracellular DNA has been introduced and thus harbors the extracellular DNA. The DNA might be introduced into the cell so that the nucleic acid is replicable either as a chromosomal integrant or as an extra chromosomal element.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e. g., E. coli plasmids col E1, pCR1, pBR322, pMB9 and their derivatives, plasmids such as RP4; phage DNAs, e. g., the numerous derivatives of phage X, e. g., NM989, and other phage DNA, e. g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences (i.e. sequences that control the expression of a DNA sequence operatively linked to it) may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage X, the control regions of fd coat protein, the promoter for 3-phosphoglycerate kinase or other glycolytic enzymes, the promoters of acid phosphatase (e. g., Pho5), the promoters of the yeast-mating factors, and other sequences known to control the expression of genes of prokaryotic or eukaryotic cells or their viruses, and various combinations thereof.

Another subject matter of the present invention is a recombinant host cell characterized in that said cell expresses a peptide or a host cell capable of expressing the isolated and purified DNA molecule as defined above, preferably a cDNA molecule, particularly a host cell which is stably transformed with an expression vector containing said DNA molecule.

The terms "host cell" and "recombinant host cell" are used interchangeably herein to indicate a eukaryotic or prokaryotic cell into which one or more DNA or vectors of the invention have been introduced. It is understood that such terms refer not only to the particular subject cell but also to the progeny or potential progeny of such a cell. Because certain modifications may occur in succeeding generations clue to either mutation or environmental influences, such progeny may not, in fact, be identical to the parent cell, but are still included within the scope of the term as used herein.

"Eukaryotic cell" refers to any mammalian or non-mammalian cell from a eukaryotic organism. By way of non-limiting example, any eukaryotic cell that is capable of being maintained under cell culture conditions and subsequently transfected would be included in this invention. Especially preferable cell types include, e. g., stem cells, embryonic stem cells, Chinese hamster ovary cells (CHO), COS, BHK21, NIH3T3, HeLa, C2C12, cancer cells, and primary differentiated or undifferentiated cells. Other suitable host cells are known to those skilled in the art.

A wide variety of unicellular host cells are useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, YB/20, NSO, SP2/0, R1. 1, B-W and L-M cells, African Green Monkey kidney cells (e. g., COS 1, COS 7, BSC1, BSC40, and BMT10), insect cells (e. g., Sf9), and human cells and plant cells in tissue culture. Preferably, the host cell is a bacterial cell, more preferably an *E. coli* cell.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large-scale animal culture.

The host cells used to produce the isolated and purified peptide of this invention may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media, described in Ham et al., 1979; Barnes et al., 1980; U.S. Pat. Nos. 4,767,704; 4,657,866; 4,927,762; 4,560,655; or 5,122,469; WO 90/03430 or WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Another subject matter of the present invention is a pharmaceutical composition comprising the isolated and purified peptide of the invention.

A further subject matter of the present invention is a pharmaceutical composition comprising as an active substance a pharmaceutically effective amount of the isolated and purified peptide as defined above, optionally in combination with pharmaceutically acceptable carriers, diluents and adjuvants. Preferably, the pharmaceutical composition of the present invention comprises pharmaceutically acceptable carriers, diluents and adjuvants: Such acceptable carriers, diluents and adjuvants should be non-toxic and should not interfere with the efficacy of the active ingredient. This pharmaceutical composition is preferably used as an agent for the preparation of a medicament for the treatment and/or prevention of inflammatory diseases, cardiovascular ischemia, pain, hyperalgesia, renal diseases, wound healing, cardiovascular ischemia, cerebral ischemia, stroke, vascular dementia, infarct dementia, myocardial ischemia, coronary heart disease, myocardial infarction, peripheral limb disease, periphery arterial occlusive disease, sepsis, wasting states, diabetes and/or disorders associated with defective blood flow or blood vessel malformation, tissue repair, stem cell differentiation, angiogenesis, lymphangiogenesis, immune system cells modulation.

The pharmaceutical composition can be in any suitable form, e.g. in the form of a solution, suspension, powder, lyophilisate, ointment or tincture. The composition can be administered by any suitable method, e.g. per injection (systemically or locally) or topically. The precise nature of the carrier or other material will depend on the route of administration, which may be oral, topical, or by injection, e.g. intravenous or intradermal.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil.

Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection.

Preservatives, stabilisers, buffers, antioxidants and/or other additives may be included, as required.

The respective pharmaceutically effect amount can depend on the specific patient to be treated, on the disease to be treated and on the method of administration. Further, the pharmaceutically effective amount depends on the specific polypeptide used, especially if the polypeptide additionally contains a cytotoxic component or not. The treatment usually comprises a multiple administration of the pharmaceutical composition, usually in intervals of several hours, days or weeks. The pharmaceutically effective amount of a dosage unit of the polypeptide usually is in the range of 0.001 ng to 100 µg per kg of body weight of the patient to be treated.

Pharmaceutical compositions used in accordance with the present invention are prepared for storage by mixing a pharmaceutically effective amount of the isolated and purified peptide as defined above having the desired degree of purity with optional pharmaceutically acceptable carriers, excipients or stabilizers (Remington's Pharmaceutical Sciences 16th edition, Osol, A. Ed. 1980), in the form of lyophilized formulations or aqueous solutions. Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN, PLURONICS or polyethylene glycol (PEG).

A further subject matter of the present invention concerns a pharmaceutical composition for use in medicine.

Another subject matter of the present invention is a pharmaceutical composition comprising the isolated and purified peptide of the invention for use as analgesics.

Preferably the pharmaceutical composition of the invention is used in the treatment and/or prevention of inflammatory diseases, cardiovascular ischemia, pain, hyperalgesia, renal diseases, wound healing, cerebral ischemia, stroke, vascular dementia, infarct dementia, myocardial ischemia, coronary heart disease, myocardial infarction, peripheral limb disease, periphery arterial occlusive disease, sepsis, wasting states, diabetes and/or disorders associated with defective blood flow or blood vessel malformation, tissue repair, stem cell differentiation, angiogenesis, lymphangiogenesis, immune system cells modulation.

In particular, the pharmaceutical composition of the invention is used in the treatment and/or prevention of inflammatory diseases, pain, hyperalgesia, cardiovascular and/or cerebral ischemic diseases, and/or disorders associated with angiogenesis, and lymphangiogenesis in a subject in need thereof.

More preferably, the pharmaceutical composition of the invention is used in the treatment and/or prevention of disorders associated with angiogenesis, and lymphangiogenesis in a subject in need thereof.

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder.

"Mammal" for purposes of treatment refers to any animal classified as a mammal, including humans, domestic and farm animals, and zoo, sports, or pet animals, such as dogs, horses, cats, cows, monkeys etc. Preferably, the mammal is human.

EXAMPLES

Example 1

In Vitro Angiogenesis Assay on Matrigel

The angiogenesis assay was performed according to the protocol described in Paschoalin T, et al (2007).

Human umbilical vein endothelial cells (HUVEC) were maintained in complete RPMI 1640 medium, pH 7.2, supplemented with 10 mM N-2-hydroxyethylpiperazine-N'-2-ethanesulphonic acid (HEPES), 24 mM sodium bicarbonate, 10% heat-inactivated fetal calf serum (FCS) from Gibco (Minneapolis, Minn., USA) and 40 µg/mL gentamicin sulfate (Hipolabor Farmacêutica, Sabará, MG, Brazil).

In vitro angiogenesis assay on Matrigel was performed as described previously (Paschoalin et al, 2007). Briefly, BD Matrigel Matrix (B&D Biosciences, Bedford, Mass., USA) was thawed on ice, distributed in 96-well plates (50 µL per well) and allowed to polymerize for 1 h at 37° C. HUVECs (15×103 cells/well) were suspended in 100 µL of RPMI medium supplemented with 2% of FCS and added to each well in the presence of peptides with possible angiogenic activity. Angiogenic stimulators and inhibitors can be incubated with the cells before adding on the Matrigel if necessary. The plates were incubated at 37° C. for 18 h and then images were captured at 8× magnification with a Sony Cyber-shot camera coupled to a light inverted microscope. The number of pro-angiogenic structures (closed rings arising from dendritic extensions of endothelial cells) was counted from 4 different wells, and the average value was determined for each sample.

When stimulated by angiogenic factors, like BK, HUVEC cells undergo the development of pro-angiogenic structures and it allows studying angiogenic or anti-angiogenic molecules. The number of pro-angiogenic structures is counted and compared to a control and to BK. Generally, peptides of the invention derived from VEGF-A were named PepA, peptides from VEGF-C were named PepC, peptides from VEGF-D were named PepD and peptides from Placental Growth Factor were named PepPl.

Figure 2:
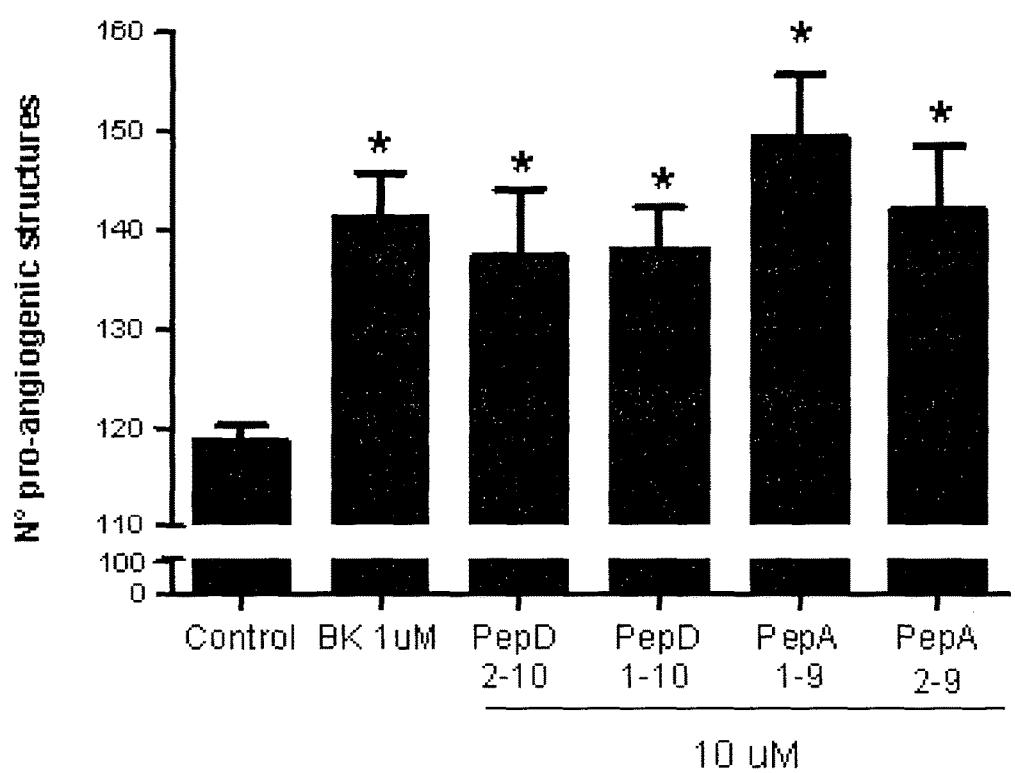
FIG. 2 shows the effect of 1 μM Bradykinin (BK) and 10 μM of the peptides PepD 2-10 (KPPCVNVFR; SEQ ID NO:8) and PepD 1-10 (SEQ ID NO:1), corresponding respectively to the aminoacid residues number 133-141 and 132-141 from human VEGF-D sequence registered at Uniprot (http://www.uniprot.org/uniprot/O43915), and PepA 1-9 (FKPSCVPLM; SEQ ID NO:20) and PepA 2-9 (KPSCVPLM; SEQ ID NO:27), corresponding to the amino acid residues number 73-81 and 74-81 from the human VEGF-A sequence registered at Uniprot (http://www.uniprot.org/uniprot/P15692), on the HUVEC angiogenesis assay. * p<0.05 compared to control (Student's "t" test).

FIG. 1 shows the result of HUVEC stimulation by PepD 2-10 (SEQ ID NO:8) at 1 µM, 10 µM and 50 µM concentrations. Results show clearly a pro-angiogenic effect at 1 and 10 µM PepD 2-10 concentrations. FIG. 2 shows the results for the same assay, now using PepD 1-10 (SEQ ID NO:1), PepD 2-10 (SEQ ID NO:8), PepA 1-9 (SEQ ID NO:20) and PepA 2-9 (SEQ ID No 27), at 10 µM concentration, compared to BK 1 µM and the control without any peptide added. Clearly PepD 1-10, PepD 2-10, PepA 1-9 and PepA 2-9 are able to induce angiogenesis.

Figure 3:
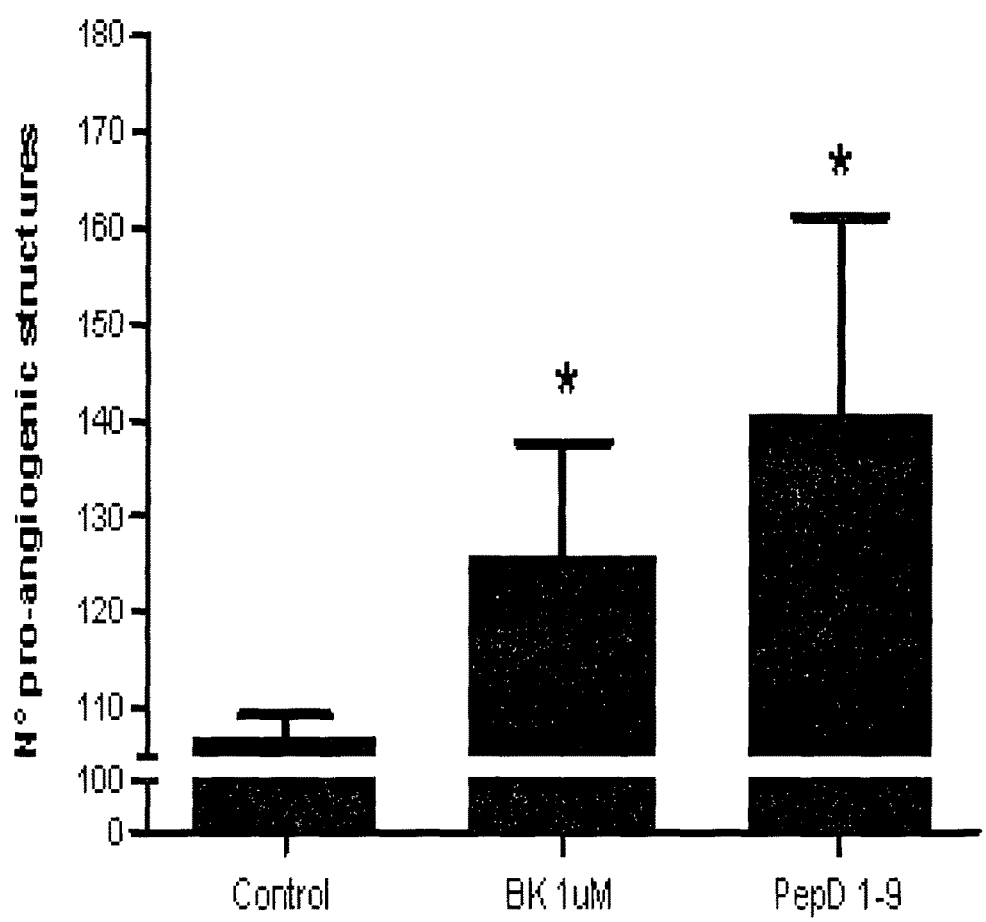
FIG. 3 shows the effect of 1 μM Bradykinin (BK) and of the peptide PepD 1-9 (FKPPCVNVF; SEQ ID NO:15), corresponding to the amino acid residues number 132-140 from human VEGF-D sequence registered at Expasy (http://www.uniprot.org/uniprot/O43915), on the HUVEC angiogenesis assay. * p<0.05 compared to control (Student's "t" test).

FIG. 3 shows the result of HUVEC stimulation by PepD 1-9 (SEQ ID NO: 15; FKPPCVVF) 10 μM compared to BK 1 μM and to the control. It shows that PepD 1-9 is able to induce angiogenesis.

Figure 4A:
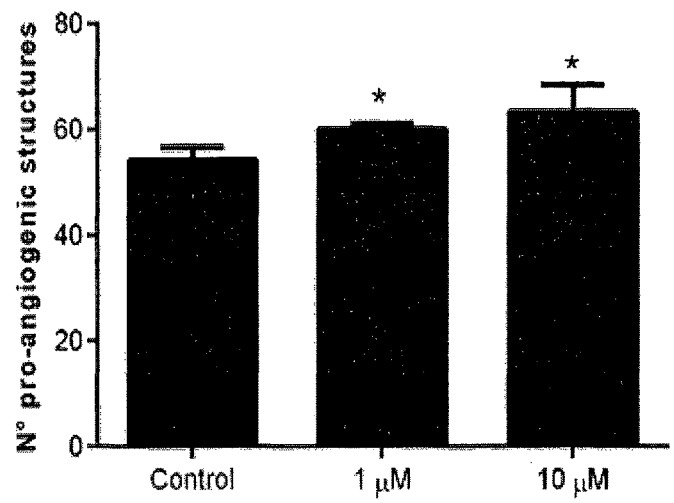
FIG. 4 shows the result of HUVEC stimulation by PepC 2-9 (FIG. 4B) and PepC 2-10 (FIG. 4A) at 1 μM and 10 μM concentrations and PepC 1-10 (FIG. 4C) at 0.1, 1.0 and 10 μM concentrations, 24 h after initial stimulus.
Figure 4B:
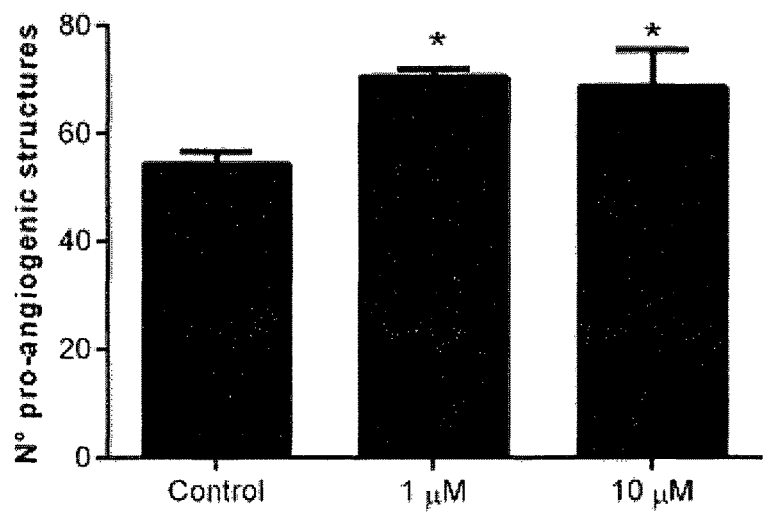
Figure 4C:
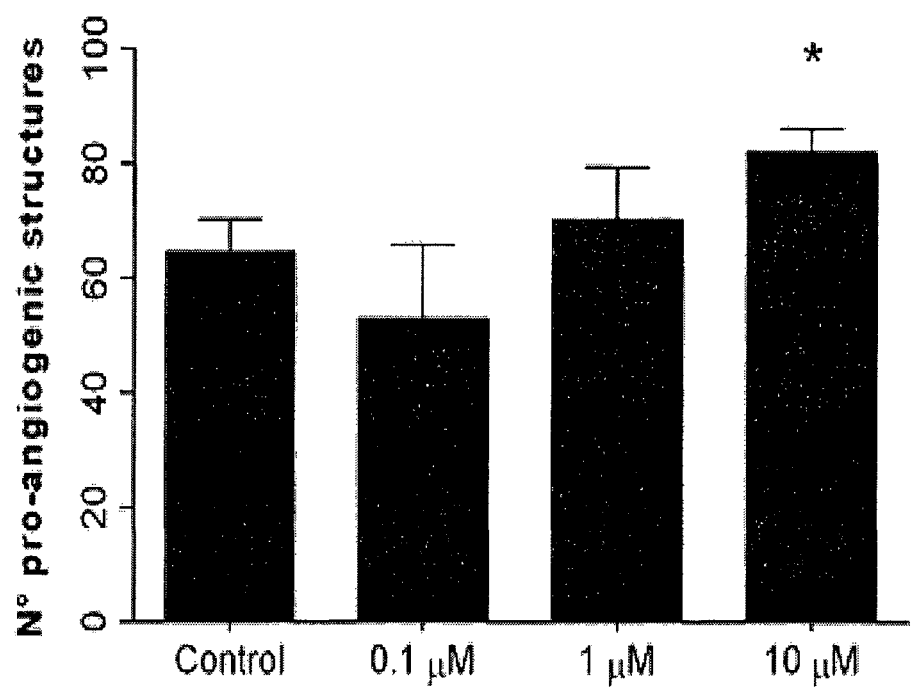

FIG. 4 shows the result of HUVEC stimulation by PepC 2-9 (FIG. 4B) and PepC 2-10 (FIG. 4A) at 1 μM and 10 μM concentrations and PepC 1-10 (FIG. 4C) at 0.1, 1.0 and 10 μM concentrations, 24 h after initial stimulus. It shows that PepC 2-9, PepC 2-10 and PepC 1-10 are able to induce angiogenesis.

* $p<0.05$, Student's "t" test, when comparing the mean number of pro-angiogenic structures from three different wells of HUVEC cultures to the control.

Example 2

Intracellular Calcium Measurement in HUVEC Cells Stimulated with PepD 2-10 Peptides The intracellular calcium measurement was performed according to the method described in Bagnaresi P et al, 2012 and Lungato L, et al., 2012.

Human umbilical vein endothelial cells were cultured in RPMI 1640 (GIBCO) containing 10% heat-inactivated fetal bovine serum (FBS), 24 mM sodium bicarbonate, 40 mg/mL gentamicin, 10 mM HEPES, pH 7.4 at 37° C. in a 5% CO2 humidified atmosphere. $5\times10^4$ cells were plated on 60 mm dishes (Costar 3260), and incubated in culture medium containing 5 μM Fluo-3 AM (Invitrogen Corporation, CA) for 40 min at 37° C. in a buffer containing the channel blocker Probenecid (40 μM), followed by 3 washes with culture medium to discard remaining extracellular probe. The cells were then placed into a culture chamber at 37° C. on the stage of a fluorescence microscope (Zeiss LSM 510 META) with excitation at 488 nm and emission at 505-530 nm. After calcium probe incubation, assays were performed with 1 uM bradykinin (BK), 10 uM PepD 2-10. To demonstrate which B receptor is activated by PepD 2-10 (KPP-CVNVFR; SEQ ID NO:8), B1 receptor antagonist Des-Arg9-Leu8-BK (10 μM) and B2 receptor antagonist HOE-140 (10 μM) where added to HUVEC cell culture for 10 min before the addition of: PepD 2-10 (10 uM) or 5 μM Thapsigargin (THG).

Fluorescence data were normalized as F/Fmax, where Fmax represents maximal intracellular fluorescence obtained with Ca2+ released from ER with addition of THG, a Ca2+ATPase inhibitor (Bagnaresi et al. 2012). THG blocks calcium pumps that recover cytosolic calcium from the cytoplasm. Under the action of THG the cytosolic calcium reaches its maximal concentration.

The software-based analysis allowed fluorescence imaging in the whole field or in a selected cell as a function of time (Image J 1.47h, NIH, USA). This was accomplished by defining areas of interest (e.g., an entire cell) on a given image frame and directing the software to construct a graphical representation of intensity over time (GraphPad Software 6 Prisma). Individual traces for typical 15 cells responses represent the intracellular calcium fluorescence changes in the analyzed cell population (Lungato et al. 2012).

FIG. 5A-E demonstrates that calcium entry in HUVEC cells induced by PepD2-10 and detected by Fluo-3 fluorescence, is due to B1 bradykinin receptor activation.

Figure 5A:
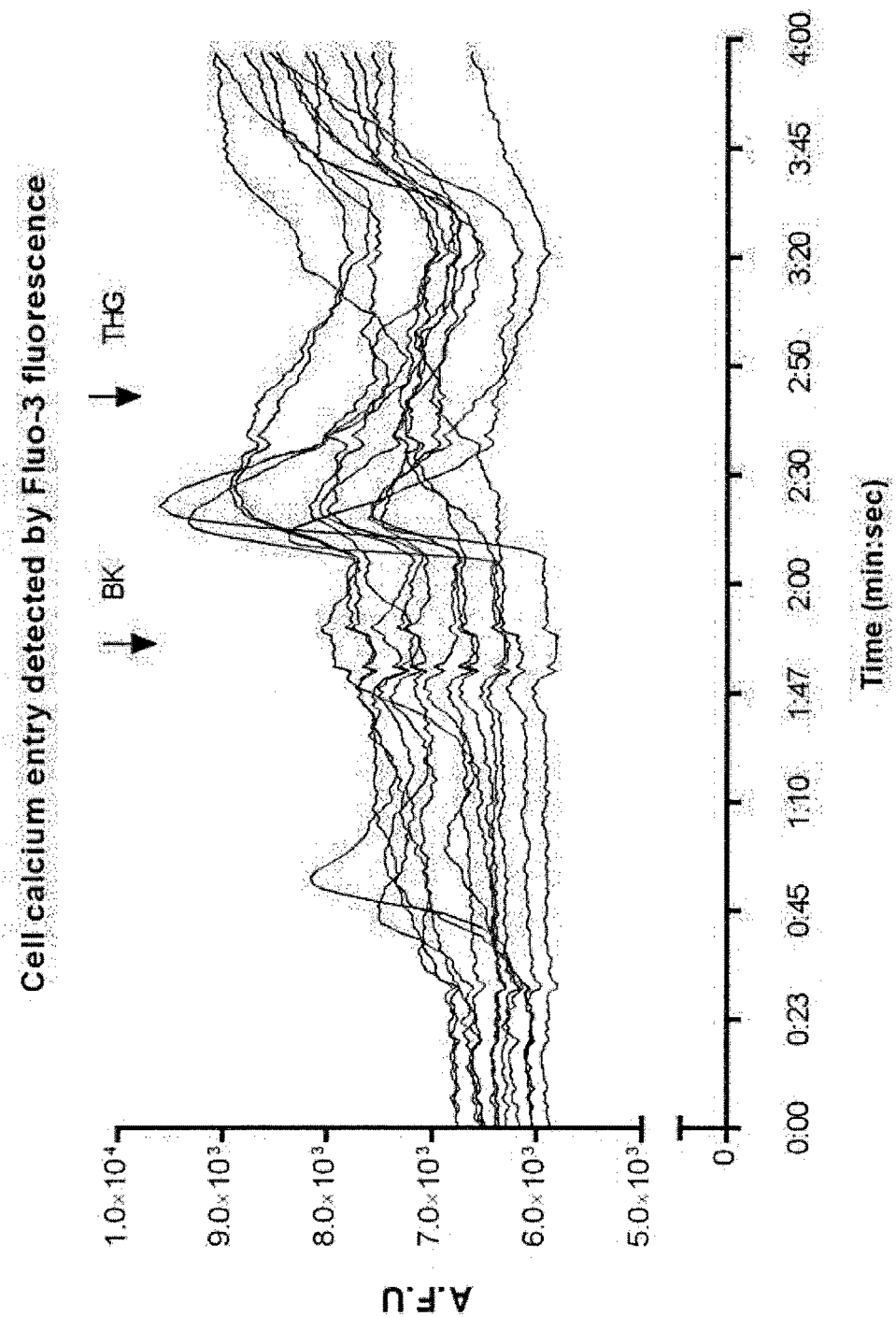
FIG. 5A-E demonstrates that Calcium entry in HUVEC cells induced by PepD2-10 and detected by Fluo-3 fluorescence, is due to B1 bradykinin receptor activation.

FIG. 5A is a control to show the effect of adding BK to HUVEC in culture (at ~1:50 min) induces calcium increase in the cytoplasm as shown by the fluorescence increase around 2:20 min. Thapsigargin added at the end allows the maximum increase of intracellular calcium to be used in ratio calculations.

Figure 5B:
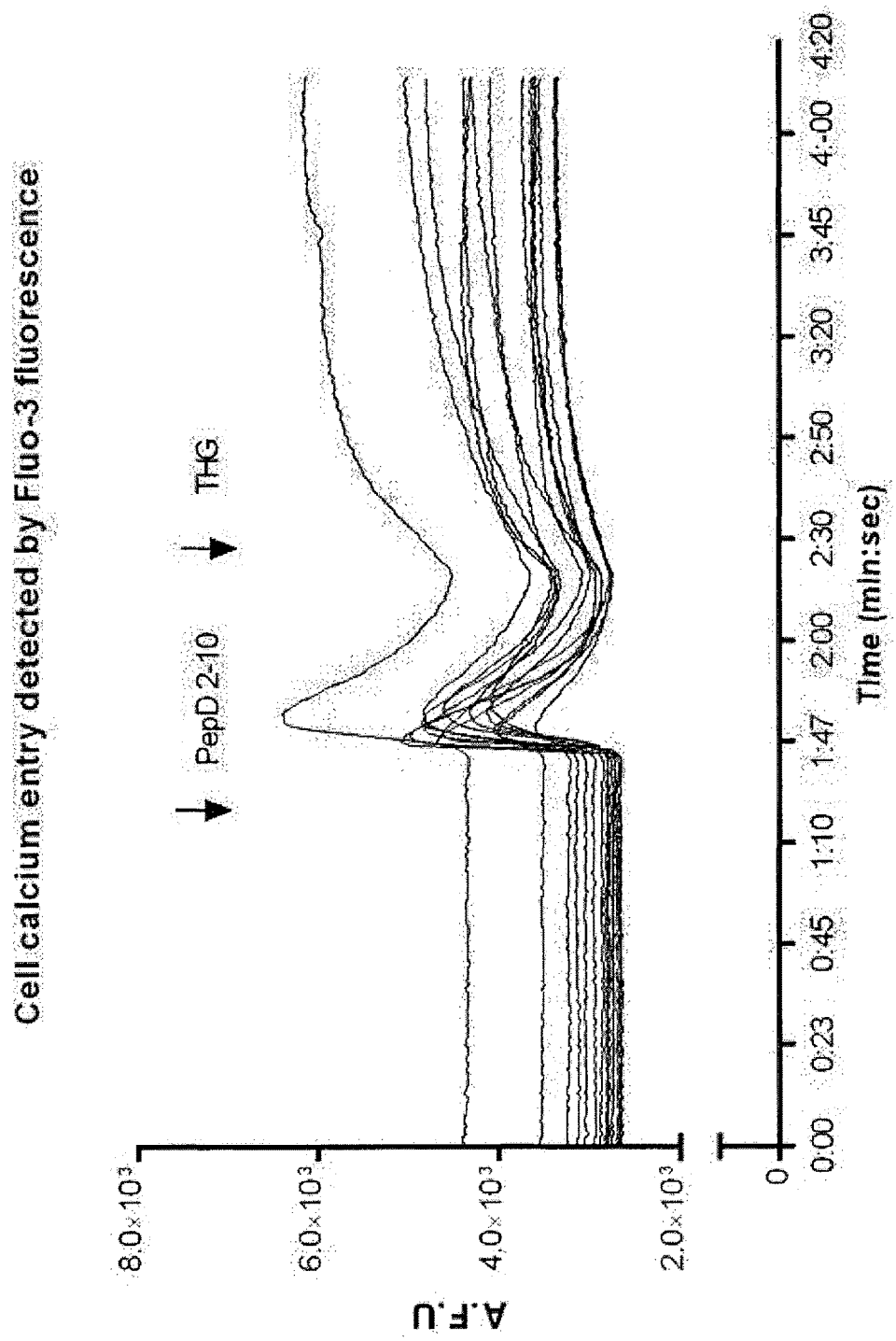
Figure 5C:
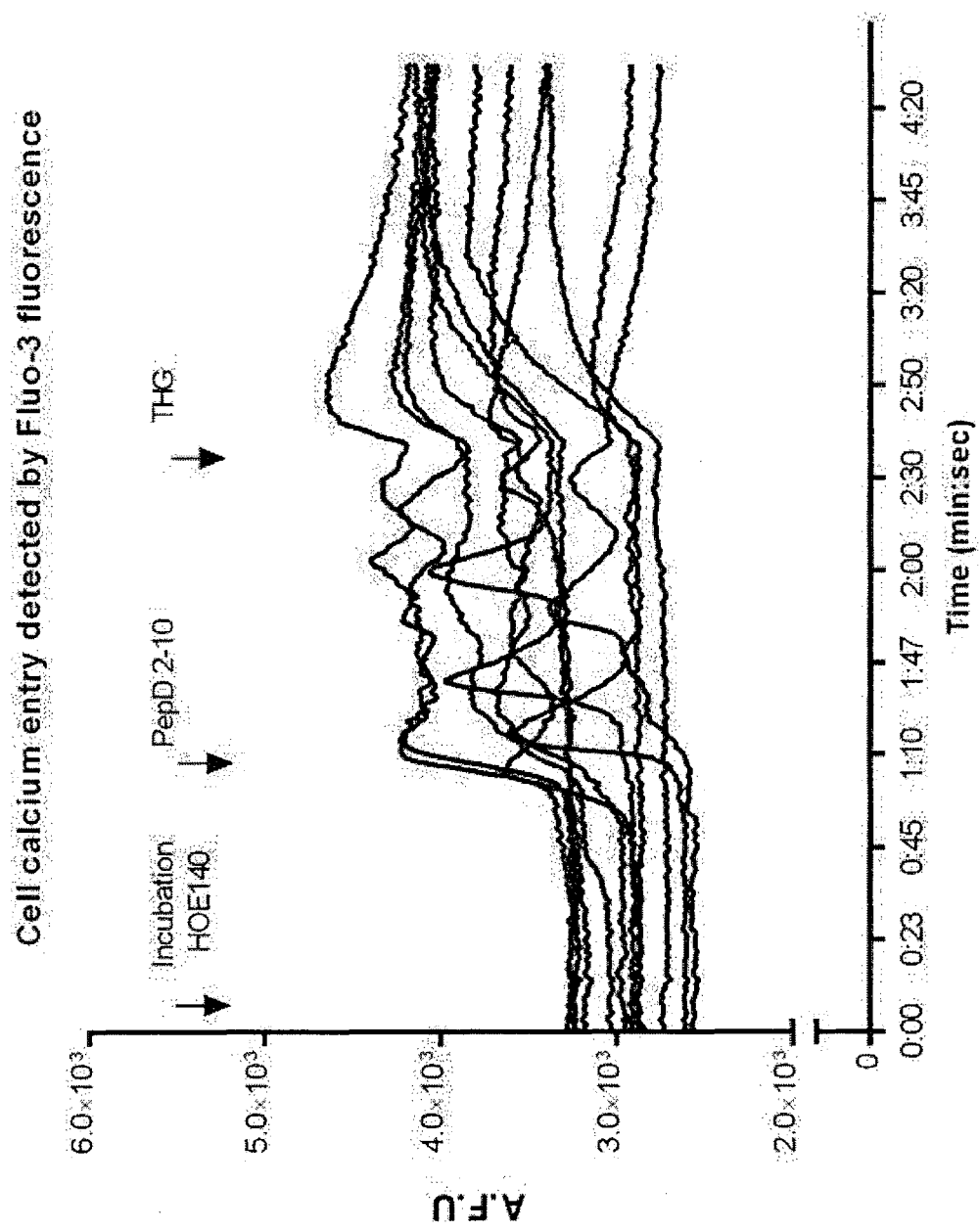
Figure 5D:
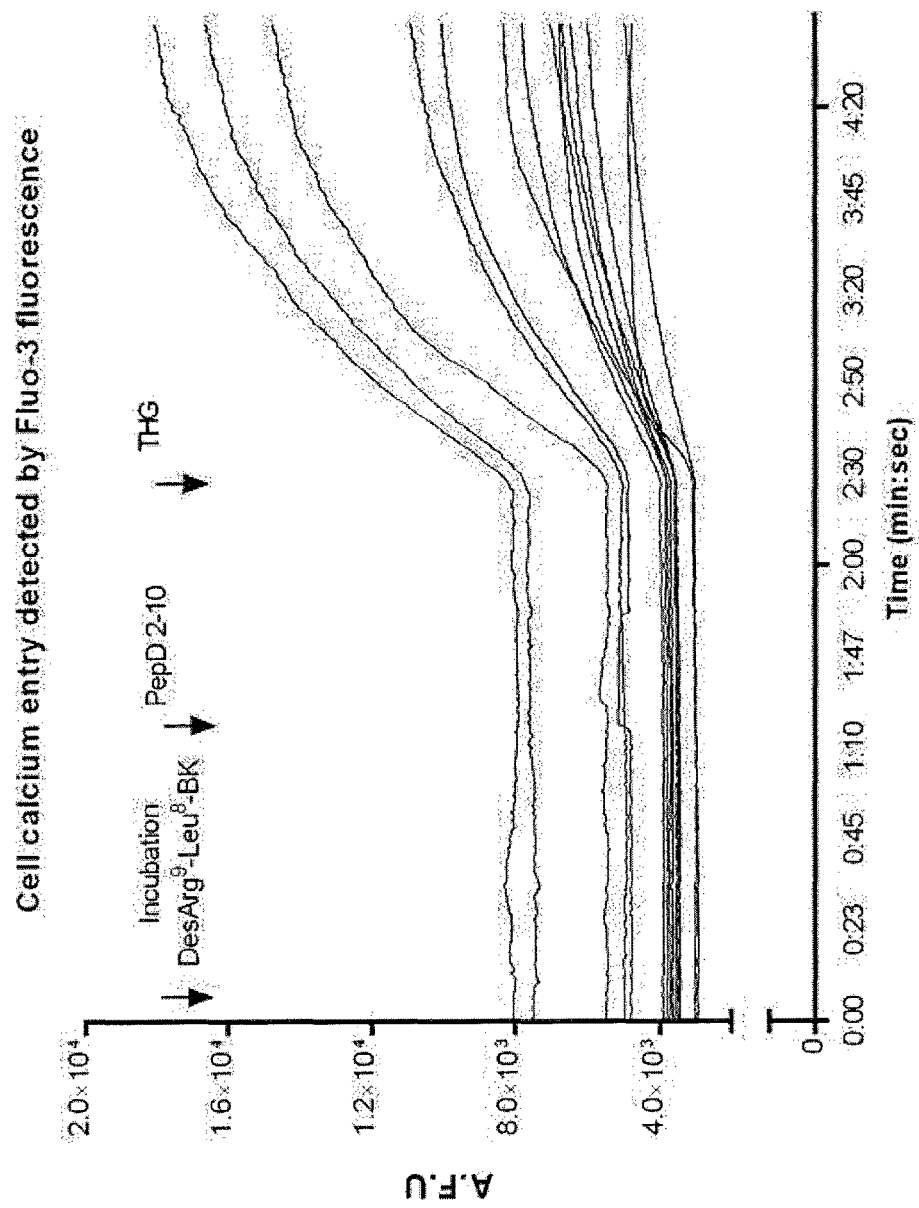

FIG. 5B shows that 10 μM PepD 2-10 also induces an increase of cytoplasmatic calcium in HUVEC cells. Previous addition of HOE140 a Bradykinin B2 receptor antagonist does not block calcium entry but clearly shows a disruption in the pattern of calcium increase, indicating the involvement of B2 receptors in the observed effect, as shown in FIG. 5C. Previous addition of DesArg9-Leu8-BK, a Bradykinin B1 receptor antagonist, completely blocks the effect of PepD 2-10, by blocking calcium entry induced by PepD 2-10 demonstrating the involvement of B1 receptor on the observed effect as shown in FIG. 5D.

Data on calcium entry indicate a B2 receptor activity (FIG. 5B) that after B2 blockage by the B2 receptor antagonist HOE140, it shows a B1 receptor activity (FIGS. 5C and 5D), that can be blocked by the B1 receptor antagonist DesArg9-Leu8-BK. It is likely that PepD 2-10 is converted to PepD 2-9. From a B2 agonist it may become a B1 agonist: PepD 2-10 is a B2 agonist (FIG. 5B), but calcium entry results shown on FIG. 5C is due to a B1 agonist activity.

|  | B2 agonist |  | B1 agonist |
|---|---|---|---|
| BK | RPPGFSPFR | DesArg9-BK | RPPGFSPF |
| PepD 2-10 | KPPCVNVFR | PepD 2-9 | KPPCVNVF |

Figure 5E:
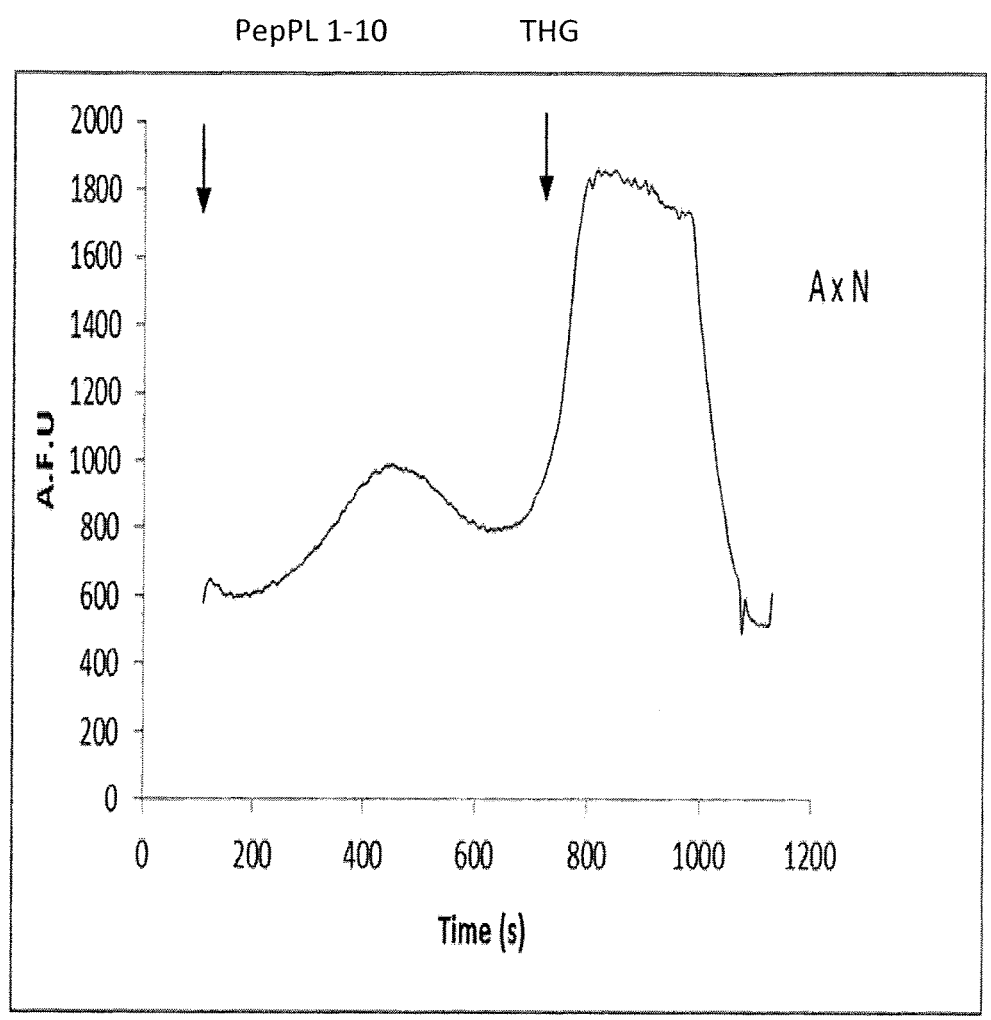

FIG. 5E shows the effect of PepPL 1-10 (SEQ ID NO:7) on cultured HUVEC cells, in the presence of the B1 receptor antagonist DesArg9-Leu8-BK, at 100 s PepPL 1-10, 10 μM is added. When applied to HUVEC cells previously treated with the fluorescent calcium indicator Fluo-3 in culture, PepPl 1-10 at 10 μM concentration induces an increase in cell fluorescence due to calcium entry in the cytoplasm. A transient fluorescence increase is observed that lasts around 5 minutes and corresponds to cytoplasmic calcium increase. Thapsigargin is then added to release all the calcium content to the cytoplasm and give a measure of the maximum fluorescence that could be expected under these conditions.

FIG. 5A: A.F.U.—Arbitrary Fluorescence Units; BK 1 μM Bradykinin; THG Thapsigargin 10 μM.

FIG. 5B: PepD 2-10 at 10 μM; THG Thapsigargin 10 μM.

FIG. 5C: HOE 140 (B2 receptor antagonist) 10 μM; PepD 2-10 10 μM; THG Thapsigargin 10 μM.

FIG. 5D: DesArg9-Leu8-BK 10 μM; PepD 2-10 10 μM; THG Thapsigargin 10 μM

FIG. 5E: AxN is the mean signal of 10 selected cells. PepPl 1-10 is the sequence derived from Placental Growth Factor (SEQ ID NO: 7; FSPSCVSLLR).

REFERENCE LIST

Bagnaresi, P., Barros, N. M. T., Assis, D. M., Melo, P. M. S., Fonseca, R. G., Juliano, M. A., Pesquero, J. B., Juliano, L., Rosenthal, P. J., Cannona, A. K., and Gazarini, M. L. (2012) Intracellular proteolysis of kininogen by malaria parasites promotes release of active kinins. Malaria Journal 11: 156.

Barnes, D., and Sato, G. (1980) Methods for growth of cultured cells in serum-free medium, Analytical Biochemistry 102, 255-270.

Cleber A. Trujillo et al., Journal of Biological Chemistry, vol. 287, No. 53, pp. 44046-44061, 2012.

Ferrara, N. (1999) Molecular and biological properties of vascular endothelial growth factor. Journal of Molecular Medicine-Jmm 77, 527-543

Ferrara, N., and DavisSmyth, T. (1997) The biology of vascular endothelial growth factor. Endocrine Reviews 18, 4-25.

Ham et al., Media and growth requirements, Meth. Enz. 58:44 (1979).

Lungato L, et al., Sleep deprivation impairs calcium signaling in mouse splenocytes and leads to a decreased immune response. Biochim Biophys Acta 1820:1997-2006 (2012).

Marceau, F., and Regoli, D. (2004) Bradykinin receptor ligands: Therapeutic perspectives. Nature Reviews Drug Discovery 3, 845-852

Paschoalin, T., Carmona, A. K.; Rodrigues, E. G., Oliveira, V., Monteiro, H. P., Juliano, M. A., Juliano, L., and Travassos, L. R. (2007) Characterization of thimet oligopeptidase and neurolysin activities in B16F10-Nex2 tumor cells and their involvement in angiogenesis and tumor growth. Molecular Cancer 6: 25-34

Sela, M., and Zisman, E. (1997) Different roles of D-amino acids in immune phenomena. Faseb Journal 11, 449-456

Trujillo, C. A., Negraes, P. D., Schwindt, T. T., Lameu, C., Carromeu, C., Muotri, A. R., Pesquero, J. B., Cerqueira, D. M., Pillat, M. M., de Souza, H. D. N., Turaca, L. T., Abreu, J. G., and Ulrich, H. (2012) Kinin-B2 Receptor Activity Determines the Differentiation Fate of Neural Stem Cells. Journal of Biological Chemistry 287, 44046-44061.

The invention claimed is:
1. An isolated peptide
having the amino acid sequence selected from the group consisting of SEQ ID NO:1 to SEQ ID NO: 5, SEQ ID NO:7, SEQ ID NO:8 to SEQ ID NO: 12, and SEQ ID NO: 14 to SEQ ID NO: 28,
wherein said isolated peptide is a Bradykinin receptor agonist; and wherein said isolated peptide is modified by chemical derivatization via acetylation or carboxylation.

2. An isolated nucleic acid molecule encoding the isolated peptide of claim 1.

3. An expression vector comprising at least one copy of the isolated and purified nucleic acid molecule of claim 2.

4. A recombinant host cell comprising the isolated and purified nucleic acid of claim 2.

5. A pharmaceutical composition comprising a therapeutically effective amount of the isolated peptide of claim 1 and a pharmaceutically acceptable carrier.

6. A recombinant host cell comprising at least one copy of the expression vector of claim 3.

7. A method of stimulating angiogenesis in a subject in need thereof, comprising administering an effective amount of the pharmaceutical composition of claim 5 to said subject.

* * * * *